United States Patent [19]

Kurono et al.

[11] Patent Number: 4,939,126
[45] Date of Patent: Jul. 3, 1990

[54] 1-PYRROLIDINEACETAMIDE DERIVATIVES AND USE THEREOF

[75] Inventors: Masayasu Kurono; Tsunemasa Suzuki; Tomoo Suzuki; Kiyotaka Hirooka; Yukiharu Matsumoto; Hiroshi Ozawa; Kiichi Sawai, all of Nagoya, Japan

[73] Assignee: Sanwa Kagaku Kenkyusho Co. Ltd., Aichi, Japan

[21] Appl. No.: 217,523

[22] Filed: Jul. 11, 1988

[30] Foreign Application Priority Data

Jul. 17, 1987 [JP] Japan .................. 62-177173

[51] Int. Cl.$^5$ .................. A61K 31/695; C07F 7/02; C07F 7/10
[52] U.S. Cl. .................. 514/63; 544/229; 548/406
[58] Field of Search .................. 514/63; 546/14; 544/229; 548/406

[56] References Cited

U.S. PATENT DOCUMENTS 3,459,738  8/1969  Morren .................. 540/531
4,476,308  10/1984  Aschwanden et al. .................. 548/406
4,678,801  7/1987  Kurono et al. .................. 548/453

Primary Examiner—Mukund J. Shah
Assistant Examiner—F. Bernhardt
Attorney, Agent, or Firm—Armstrong, Nikaido, Marmelstein, Kubovcik & Murray

[57] ABSTRACT

1-Pyrrolidineacetamide derivatives of the formula

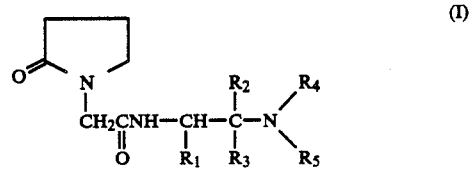
(I)

wherein $R_1$ is hydrogen atom or a trialkylsilyl group, $R_2$ and $R_3$ are hydrogen atom, respectively, when $R_1$ is hydrogen atom, $R_4$ is an alkyl group, $R_5$ is a radical of

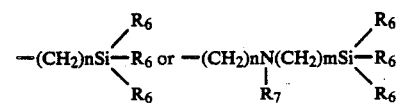

in which $R_6$ and $R_7$ are an alkyl group, respectively, m and n are an integer of 1 to 3, respectively, or $R_4$ represents together with $R_5$ a hetero cyclic ring having nitrogen and silicon atoms or piperazine ring having a substituent of

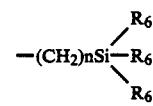

in which $R_6$ and n have the meanings as referred to, and $R_2$ and $R_4$ as well as $R_3$ and $R_5$ form a hetero cyclic ring, respectively, connected with an alkylene chain, where $R_1$ is the trialkylsilyl group, salts thereof, a process for the preparation thereof, as well as use thereof as for a medicine.

10 Claims, No Drawings

1-PYRROLIDINEACETAMIDE DERIVATIVES AND USE THEREOF

BACKGROUND OF THE INVENTION

1. Field of the Invention

The present invention relates to novel 1-pyrrolidineacetamide derivatives, salts thereof, a process for the preparation of the compounds thereof and use of same in the pharmaceutical field and more particularly, as an effective ingredient for the medicine to prevent or cure a cerebral dysfunction.

2. Related Arts

Hitherto, various studies have been made on γ-amino butyric acid (GABA) and its derivatives to seek for an effective ingredient of the medicine for preventing and curing a cerebral dysfunction. By the way of the studies, 2-oxo-1-pyrrolidineacetamide [Piracetam; 2-(Pyrrolidin-2-on-1-yl)acetamide] has been discovered to draw a remarkable attention but higher pharmaceutical effects as initially expected have not been proved through actual clinical tests.

However, various studies on derivatives of this compound has been continued and some of the present inventors have also proposed following 2-oxopyrrolidine compounds in Jap. Pat. No. 62 - 22785 (A) (corresponding to U.S. Pat. No. 4,678,801 and EP-A2-0213713).

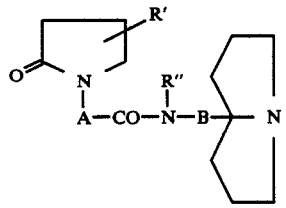

wherein R' and R" are hydrogen atom or an alkyl group, respectively, A is an alkylene group or phenyl substituted alkylene group, and B is an alkylene group.

SUMMARY OF THE INVENTION

A primary object of the invention is to provide an effective ingredient for the medicine for preventing and curing a cerebral dysfunction, which can be substituted for the Piracetam and is different from the compounds disclosed in said patents.

A secondary object of the invention is to provide a process for preparing compounds which are effective for preventing and curing the cerebral dysfunction.

A tertiary object of the invention is to provide a pharmaceutical composition comprising at least one of the compounds to prevent or cure the cerebral dysfunction.

According to the invention, the above and other objects can basically be attained by a 1-pyrrolidineacetamide derivative of the formula

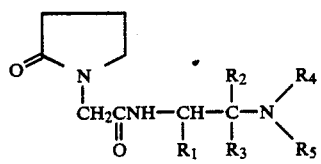

wherein $R_1$ is hydrogen atom or a trialkylsilyl group, $R_2$ and $R_3$ are hydrogen atom, respectively, when $R_1$ is hydrogen atom, $R_4$ is an alkyl group, $R_5$ is a radical of

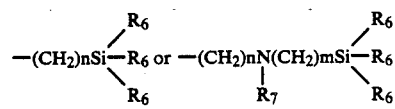

in which $R_6$ and $R_7$ are an alkyl group, respectively, m and n are an integer of 1 to 3, respectively, or $R_4$ represents together with $R_5$ a hetero cyclic ring having nitrogen and silicon atoms or piperazine ring having a substituent of

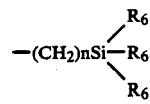

in which $R_6$ and n have the meanings as referred to, and $R_2$ and $R_4$ as well as $R_3$ and $R_5$ form a hetero cyclic ring, respectively, connected with an alkylene chain, when $R_1$ is the trialkylsilyl group, or a salt thereof.

Because the compounds (I) and salts thereof have an excellent cerebral function protecting action.

In the compounds of Formula (I), trimethylsilyl, triethylsilyl, t-butyldimethylsilyl or the like may be listed as the "trialkylsilyl group". As the "heterocyclic ring", wherein $R_2$ and $R_4$ as well as $R_3$ and $R_5$ are connected with alkylene chain, 1-azabicyclo[3,3,0]octane ring, 1-azabicyclo[4,4,0]decane ring or the like may be listed. As the "alkyl group", methyl, ethyl, propyl, isopropyl, butyl, t-butyl, pentyl or the like radical may be listed. As the "heterocyclic ring having nitrogen and silicon atoms", 4,4-dimethyl-1-aza-4-silacyclohexane ring, 4,4-diethyl-1-aza-4-silacyclohexane ring, 3,3-dimethyl-1-aza-3-silacyclopentane ring or the like may be listed.

According to the process of the invention, the compounds of Formula (I) and salts thereof can be prepared, in accordance with one of following synthetic routes.

Rout 1

A process, wherein a compound of the formula

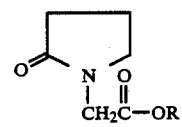

wherein R is hydrogen atom or a lower alkyl group, is reacted with another compound of the formula

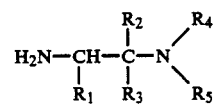

wherein $R_1$, $R_2$, $R_3$, $R_4$ and $R_5$ have the meanings as referred to, and if necessary, converting the reaction product into the salt.

In this synthetic route, it is preferable to compose the raw materials (II) and (III) in a molar ratio of about 1:0.8 to 1:1.5. The reaction proceeds at a temperature of 50°–150° C. and in the presence or absence of a solvent. As the solvent, methanol, ethanol, isopropanol or the like alcohol; benzene, toluene or the like aromatic hydrocarbon; dimethylformamide or the like aprotic polar solvent; methylene chloride, chloroform or the like chlolinic solvent; diethylether, tetrahydrofuran or the like ether may be listed. An isolation and purification of an objective compound from the reaction mixture can be carried out through concentration, extraction, column chromatography, recrystallization or the like conventional operation.

Route 2

A process, wherein a compound of the formula

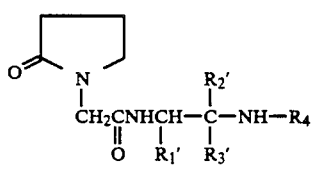 (IV)

wherein $R_1'$, $R_2'$ and $R_3'$ are hydrogen atom, respectively, and $R_4$ has the meaning as referred to, is reacted with another compound of the formula,

X-R$_5$(V)

wherein $R_5$ has the meaning as referred to, and X is a halogen atom, and if necessary, converting the reaction product into the salt.

The reaction can be carried out, in the presence of a basic compound of, for instance, triethylamine, Hüenig base or the like organic compound; sodium hydroxide, potassium carbonate, sodium carbonate, sodium hydrogen carbonate or the like. In this case, it is preferable to compose the raw materials (IV) and (V) as well as the base compound in molar ratio of 1:0.8:0 to 1:5:30 . The reaction conditions, solvent and operation procedure for this Route are similar to those for said Route 1.

Route 3

A process, wherein a compound of the formula

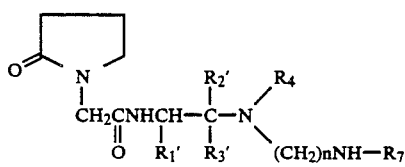 (VI)

wherein $R_1'$, $R_2'$, $R_3'$, $R_4$, $R_7$ and n have the meanings as referred to, is reacted with another compound of the formula,

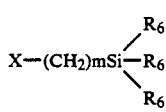 (VII)

wherein $R_6$, m and X have the meanings as referred to, and if necessary, converting the reaction product into the salt.

The reaction can be carried out, also in the presence of a basic compound as referred to on the Route 2. A molar ratio of the raw materials (VI) and (VII) as well as the basic compound is similar to that in Route 2. and the reaction conditions, solvent and operation procedure are similar to those in Route 1.

Route 4

A process, wherein a compound of the formula

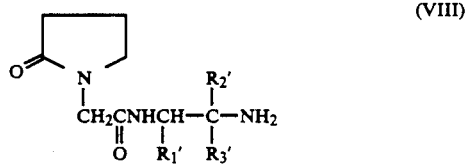 (VIII)

wherein $R_1'$, $R_2'$, and $R_3'$ have the meanings as referred to, is reacted with another compound of the formula,

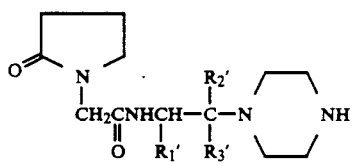 (IX)

wherein $R_6$ and X have the meanings as referred to, and o and p are an integer of 1 to 3, respectively, and if necessary, converting the reaction product into the salt.

The reaction can be carried out, also in the presence of a basic compound as referred to on the Route 2. In this case, it is preferable to compose the raw materials (VIII) and (IX) as well as the basic compound in molar ratio of 1:0.4:0 to 1:2.5:30. The reaction conditions, solvent and operation procedure for this Route are similar to those in Route 1.

Route 5

A process, wherein a compound of the formula

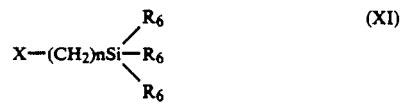 (X)

wherein $R_1'$, $R_2'$ and $R_3'$ have the meanings as referred to, is reacted with another compound of the formula, $$X-(CH_2)_mSi\begin{matrix}R_6\\R_6\\R_6\end{matrix}$$ (XI)

wherein $R_6$, X and n have the meanings as referred to, and if necessary, converting the reaction product into the salt.

The reaction can be carried out, also in the presence of a basic compound as referred to on the Route 2. In this case, molar ratio of the raw materials (X) and (XI) as well as the basic compound may be of same with the case for Route 2. Thereaction conditions, solvent and operation procedure for this Route are similar to those in Route 1.

The compounds and salts according to the invention can be made into a medicine which comprises at least one of those as an effective ingredient. There is no limitation in form of the medicine and thus it may be made into a tablet, pill, hard capsule, soft capsule, powder, granule, suppositry or the like solid preparation, or a solution, suspension, emulsion or the like liquid preparation.

A dosing amount of the compound or salt depends on various factors such as a kind of the compound or salt to be selected, form of the preparation as medicine, kind and state of disease, age and state of a patient and others but for an adult, it is preferable to give 1 to 1000 mg/day and more particularly 10 to 100 mg/day.

PREFERRED EMBODIMENTS OF THE INVENTION

The invention will now be further explained with reference to Examples for preparing compounds and salts, Pharmacological Test Example and Examples for preparing medicines.

Example 1

2-Oxo-N-[(pyrrolizidin-7a-yl)(trimethylsilyl)methyl]-1-pyrrolidineacetamide

A mixture of 150 mg (0.706 mmol) of 7a-[(amino)(trimethylsilyl)methyl]pyrrolizidine and 133 mg (0.777 mmol) of ethyl 2-oxo-1-pyrrolidineacetate was stirred at 80° C. for 5 hours. After cooled, the reaction mixture was chromatographed on alumina column to afford 95.3 mg
(Yield: 40.0%) of the desired compound as colorless oil.

Mass spectrum (EI/DI) m/z: 322 ($M^+$ −15), 110 (base peak).

$^1$H-NMR spectrum (CDCl$_3$) δ ppm: 0.07 (9H, s); 1.00–3.23 (17H, m); 3.50–3.77 (2H, m); 4.10 (2H, s); 6.75 (1H, brd).

IR spectrum ($\nu_{max}^{solution}$) cm$^{-1}$: 2950, 2880, 1670.

Example 2

N-[2-[(isopropyl)(trimethylsilylmethyl)amino]ethyl]-2-oxo-1-pyrrolidineacetamide A mixture of 5.00 g (22.0 mmol) of N-[2-(isopropylamino)ethyl]-2-oxo-pyrrolidineacetamide, 8.10 g (66.0 mmol) of trimethylsilylmethyl chloride, 30 ml of triethylamine and 50 ml of N,N-dimethylformaide was stirred at 150° C. for 24 hours in a shield tube. After cooled, the reaction mixture was concentrated in vacuo and chromatographed the residue on alumina column to afford 3.5 g (Yield: 51.3%) of the desired compound as colorless oil.

Mass spectrum (EI/DI) m/z: 313 ($M^+$), 298 ($M^+$ −15), 158 (base peak).

$^1$H-NMR spectrum (CDCl$_3$) δ ppm: −0.06 (9H, s); 0.85 (6H, d); 1.84 (2H, s); 2.15–3.68 (11H, m); 3.85 (2H, s); 6.44 (1H, brs).

IR spectrum ($\nu_{max}^{neat}$) cm$^{-1}$: 3250, 3100, 2960, 1700, 1650, 850.

Example 3

N-[2-[(isopropyl)[2-[(methyl)(trimethylsilylmethyl)amino]ethyl]amino]ethyl]-2oxo-1-pyrrolidineacetamide A mixture of 8.71 g (30.7 mmol) of N-[2-[(isopropyl)[2-(methylamino)ethyl]amino]ethyl]-2-oxo-1-pyrrolidineacetamide and 3.76 g (30.7 mmol) of trimethylsilylmethyl chloride was stirred at 80°–90° C. for 30 hours. The reaction mixture was neutralized with methanol solution of NaOH and concentrated in vacuo. The residue was chromatographed on alumina column and distilled in vacuo to afford 3.20 g (Yield: 28.1%) of the desired compound.

Boiling point: 90°–96° C. (0.6 mmHg)

Mass spectrum (EI/DI) m/z: 370 ($M^+$), 355 ($M^+$ −15), 240 (base peak)

$^1$H-NMR spectrum (CDCl$_3$) δ ppm: −0.03 (9H, s); 0.90 (6H, d); 1.84 (2H, s); 2.0–3.6 (15H, m); 2.19 (3H, s); 3.87 (2H, s); 7.10 (1H, brs).

IR spectrum ($\nu_{max}^{neat}$) cm$^{-1}$: 3300, 2960, 1670, 1250, 850.

Example 4

N-[2-[(isopropyl)[2-[(methyl)[2-(trimethylsilyl)ethyl]amino]ethyl]amino]ethyl]-2-oxo-1-pyrrolidineacetamide A mixture of 2.48 g (8.73 mmol) of N-[2-(isopropyl)[2-(methylamino)-ethyl]amino]ethyl]-2-oxo-1-pyrrolidineacetamide and 1.74 g (9.61 mmol) of 2-bromoethyltrimethylsilane was stirred at 80°–90° C. for 1 hour. The reaction mixture was neutralized with methanol solution of NaOH and concentrated in vacuo. The residue was chromatographed on alumina column and distilled in vacuo to afford 1.20 g (Yield: 35.8%) of the desired compound.

Boiling point: 140°–150° C. (0.5 mmHg)

Mass spectrum (EI/DI) m/z: 369 ($M^+$ −15), 240 (base peak)

$^1$H-NMR spectrum (CDCl$_3$) δ ppm: −0.12 (9H, s); 0.4–0.8 (2H, m); 0.88 (6H, d); 1.7–3.6 (17H, m); 2.11 (3H, s); 3.81 (2H, s); 7.35 (1H, brs).

IR spectrum ($\nu_{max}^{neat}$) cm$^{-1}$: 3300, 2960, 1670, 1250, 860.

Example 5

N-[2-(4,4-dimethyl-1-aza-4-sila-1-cyclohexyl)ethyl]-2-oxo-1-pyrrolidineacetamide A mixture of 1.90 g (10.3 mmol) of N-(2-aminoethyl)-2-oxo-1-pyrrolidineacetamide, 2.76 g (10.1 mmol) of bis(2-bromoethyl)dimethylsilane, 5.20 g of Huenig base, and 20 ml of chloroform was stirred and then the solvent was removed in vacuo. The resulting mixture was heated at 100°–105° C. for 8 hours. Aqueous NaHCO$_3$ was added to the cooled reaction mixture, and the aqueous solution was extracted with chloroform. The dried chloroform solution was concentrated in vacuo and chromatographed on silica gel column to afford 450 mg (Yield: 15.0%) of the desired compound.

Mass spectrum (EI/GC) m/z: 297 ($M^+$), 282 ($M^+$ −15), 142 (base peak).

$^1$H-NMR spectrum (CDCl$_3$) δ ppm: 0.12 (6H, s); 0.94 (4H, t); 2.03–2.63 (4H, m); 2.65–3.28 (6H, m); 3.55–3.73 (4H, m); 4.01 (2H, s); 7.55 (1H, brs).

IR spectrum ($\nu_{max}^{neat}$) cm$^{-1}$: 3300, 2970, 1690, 1660, 1250.

Example 6

2-Oxo-N-[2-[4-[2-(trimethylsilyl)ethyl]-1-piperazinyl]ethyl]-1-pyrrolidineacetamide and its hydrochloride A mixture of 14.8 g (58.3 mmol) of 2-oxo-N-(2-piperazinylethyl)-1-pyrrolidineacetamide, 16.1 g (117 mmol) of K$_2$CO$_3$, 10.6 g (58.3 mmol) of 2-bromoethyltrimethylsilane and 100 ml of toluene was stirred at 105° C. for 2 hours. The reaction mixture was filtrated, concentrated in vacuo, and chromatographed on alumina column to afford 10.6 g (Yield: 53.0%) of the desired compound, as colorless oil. Treatment of this oil with HCl in diethylether gave corresponding salt having following physical properties.

Melting point: 180°–190° C. (dec.).

Mass spectrum (EI/DI) m/z: 354 (M+), 199 (base peak).

$^1$H-NMR spectrum (CD$_3$OD) δ ppm: 0.17 (9H, s); 1.0–1.3 (2H, m); 2.0–3.8 (20H, m); 4.09 (2H, s).

IR spectrum ($\nu_{max}^{KBr}$) cm$^{-1}$: 3450, 3300, 2950, 2550, 1670, 1250.

Example 7

2-Oxo-N-[2-[4-[3-(trimethylsilyl)propyl]-1-piperazinyl]ethyl]-1-pyrrolidineacetamide and its hydrochloride A mixture of 20.8 g (82.0 mmol) of 2-oxo-N-(2-piperazinylethyl)-1-pyrrolidineacetamide, 22.6 g (164 mmol) of K$_2$CO$_3$, 12.4 g (82.0 mmol) of 3-chloropropyl-trimethylsilane and 100 ml of toluene was stirred at 105° C. for 20 hours. The reaction mixture was filtrated, concentrated in vacuo, and chromatographed on alumina column to afford 14.5 g (Yield: 48.3%) of the desired compound, as colorless oil. Treatment of this oil with HCl in diethylether gave corresponding salt having following physical properties.

Melting point: 131°–134° C.

Mass spectrum (EI/DI) m/z: 368 (M+), 213 (base peak).

$^1$H-NMR spectrum (CD$_3$OD) δ ppm: 0.07 (9H, s); 0.4–0.8 (2H, m); 1.5–3.7 (22H, m); 4.04 (2H, s).

IR spectrum ($\nu_{max}^{KBr}$) cm$^{-1}$: 3400, 3300, 2950, 2550, 1660, 1250.

Pharmacological Test Example

(a) Subject or purpose

A study was made to check preclinical profile of test compounds by determining these effects on memory retrieval in a test of passive avoidance, in which retention of the avoidance response decreases with the passage of time.

(b) Animals

Male ICR mice were used.

(c) Apparatus

The apparatus is a training box consisting of two-compartments divided by a gate into a lightened chamber and darkened chamber. The darkened chamber was made up of electrifiable grid floor and shock was delivered to the animal's feet with a shock generator-scrambler.

(d) Method

On the training day (acquisition test), each mouse was placed in the lightened chamber, starting a stop-watch. The moment when the mouse stepped through to the darkened chamber, stopping the watch and foot shock was given until he backs to the lightened chamber. The mouse was then removed promptly from the apparatus to his home cage.

Twenty-four hours after the training (retention test), each mouse was placed into the lightened chamber, and step-through latency was measured. This response latency was timed to an arbitary maximum of 300 seconds. Test compounds were given 10 mg/kg p.o. 30 min. before acquisition trial. For memory disruption, mice were given 120 mg/kg intraperitoneal injection of cycloheximide 15 min. before acqusitior test.

(e) Data analysis

The means of the latencies in seconds to enter the dakened chamber during the retention tests were compared for treated and vehicle control groups. Values were indicated prolongation percent in retention time. The followings were results of this study.

| Test compounds | Heads | Prolongation |
|---|---|---|
| Example 1 | 15 | 27.8 (%) |
| Example 2 | 15 | 28.2 |
| Piracetam | 15 | 21.7 |
| Aniracetam | 15 | −1.0 |

Medicine Preparation Example 1 (Tablet)

Following ingredients were composed to prepare tablets in a conventional manner.

| | |
|---|---|
| Compound (Example 6, hydrochloride) | 20 (mg) |
| Lactose | 115 |
| Hydroxypropylcellulose | 8 |
| Corn starch | 7 |
| | 150 mg/tablet |

Medicine Preparation Example 2 (Capsule)

Following ingredients were composed and filled in hard gelatin capsules in a conventional manner.

| | |
|---|---|
| Compound (Example 6, hydrochloride) | 20 (mg) |
| Lactose | 147 |
| Magnesium stearate | 3 |
| | 170 mg/capsule |

What is claimed is:

1. A 1-pyrrolidineacetamide derivative of the formula

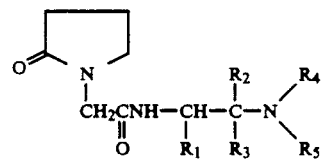

(I)

wherein R$_1$ is hydrogen or trialkylsilyl; when R$_1$ is hydrogen, R$_2$ and R$_3$ are hydrogen; R$_4$ is alkyl having 1 to 5 carbon atoms, R$_5$ is

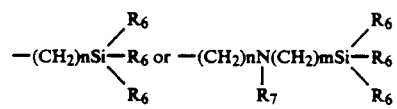

in which R$_6$ and R$_7$ are alkyl having 1 to 5 carbon atoms, m and n are each an integer of 1 to 3, or R$_4$ together with R$_5$ and the nitrogen atom to which R$_4$ and R$_5$ are bonded forms a heterocyclic ring selected from the group consisting of 4,4-dimethyl-1-aza-4-silacyclohexane, 4,4-diethyl-1-aza-4-silacyclohexane and 3,3-dimethyl-1-aza-3-silacyclopentane, or forms a piperazine ring having a

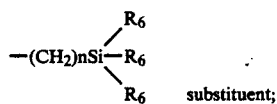
substituent;

when $R_1$ is trialkylsilyl, $R_2$, $R_3$, $R_4$ and $R_5$ together with the nitrogen atom to which $R_4$ and $R_5$ are bonded form a heterobicyclic ring selected from the group consisting of 1-azabicyclo[3,3,0]octane and 1-azabicyclo[4,4,0]decane; or a pharmaceutically acceptable salt thereof.

2. A 1-pyrrolidineacetamide derivative or a pharmaceutically acceptable salt thereof as claimed in claim 1, wherein said derivative is N-[2-[(isopropyl)(trimethylsilylmethyl)amino]ethyl]-2-oxo-1-pyrrolidineacetamide.

3. A 1-pyrrolidineacetamide derivative or a pharmaceutically acceptable salt thereof as claimed in claim 1, wherein said derivative is N-[2-[(isopropyl)[2-[(methyl)-(trimethylsilylmethyl)amino]ethyl]-2-oxo-1-pyrrolidineacetamide.

4. A 1-pyrrolidineacetamide derivative or a pharmaceutically acceptable salt thereof as claimed in claim 1, wherein said derivative is N-[2-[(isopropyl)[2-[(methyl)[2-(trimethylsilyl)ethyl]amino]ethyl]amino]ethyl]-2-oxo-1-pyrrolidineacetamide.

5. A 1-pyrrolidineacetamide derivative or a pharmaceutically acceptable salt thereof as claimed in claim 1, wherein said derivative is N-[2-(4,4-dimethyl-1-aza-4-sila-1-cyclohexyl)ethyl]-2-oxo-1-pyrrolidineacetamide.

6. A 1-pyrrolidineacetamide derivative or a pharmaceutically acceptable salt thereof as claimed in claim 1, wherein said derivative is 2-oxo-N-[2-[4-[2-(trimethylsilyl)ethyl]-1-piperazinyl]ethyl]-1-pyrrolidineacetamide.

7. A 1-pyrrolidineacetamide derivative or a pharmaceutically acceptable salt thereof as claimed in claim 1, wherein said derivative is 2-oxo-N-[2-[4-[3-(trimethylsilyl)propyl]-1-piperazinyl]ethyl]-1-pyrrolidineacetamide.

8. A 1-pyrrolidineacetamide derivative or a pharmaceutically acceptable salt thereof as claimed in claim 1, wherein said derivative is 2-oxo-N-[(pyrrolizidin-7a-yl)-(trimethylsilyl)methyl]-1-pyrrolidineacetamide.

9. A pharmaceutical composition for enhancing memory which comprises a memory enhancing effective amount of a compound according to claim 1 together with a pharmaceutically acceptable carrier.

10. A pharmaceutical composition as claimed in claim 9 wherein said 1-pyrrolidineacetamide derivative is at least one of those selected from the group consisting of
(a) N-[2-[(isopropyl)(trimethylsilyl-methyl)amino]ethyl]-2-oxo-1-pyrrolidineacetamide,
(b) N-[2-[(isopropyl)[2-[(methyl)(trimethylsilylmethyl)amino]ethyl]amino]ethyl]-2-oxo-1-pyrrolidineacetamide,
(c) N-[2-[(isopropyl)[2-[(methyl)[2-(trimethylsilyl)ethyl]amino]ethyl]amino]ethyl]-2-oxo-1-pyrrolidineacetamide,
(d) N-[2-(4,4-dimethyl-1-aza-4-sila-1-cyclohexyl)ethyl]-2-oxo-1-pyrrolidineacetamide,
(e) 2-oxo-N-[2-[4-[2-(trimethylsilyl)ethyl]-1-piperazinyl]ethyl]-1-pyrrolidineacetamide,
(f) 2-oxo-N-[2-[4-[3-(trimethylsilyl)propyl]-1-piperazinyl]ethyl]-1-pyrrolidineacetamide, and
(g) 2-oxo-N-[(pyrrolizidin-7a-yl)(trimethylsilyl)methyl]-1-pyrrolidineacetamide.

* * * * *